US00PP12283P2

(12) United States Plant Patent
Chang

(10) Patent No.: US PP12,283 P2
(45) Date of Patent: Dec. 18, 2001

(54) STRAWBERRY PLANT CALLED 'RUBY'

(76) Inventor: Peggy Pai-Chi Chang, 5983 Green Blvd., Naples, FL (US) 34116

( * ) Notice: Subject to any disclaimer, the term of this patent is extended or adjusted under 35 U.S.C. 154(b) by 0 days.

(21) Appl. No.: 09/497,677

(22) Filed: Feb. 4, 2000

(51) Int. Cl.[7] ..... A01H 5/00
(52) U.S. Cl. ..... Plt./208
(58) Field of Search ..... Plt./208, 209

*Primary Examiner*—Bruce R. Campell
*Assistant Examiner*—Susan B. McCormick

(57) ABSTRACT

'Ruby' is a new and distinct short-day cultivar of strawberry plant, which produces large conic shape, glossy red color, sweet, juicy and firm fruits. The production is higher than 'Camarosa' and the semi-early maturity is similar to 'Camarosa' when grown in central and south Florida. 'Ruby' plant has the characteristics of low chilling requirement, open plant type, long fruit stem, easy harvesting characteristics which is adapted to growing in the major fruit production areas of the Southeastern United States.

2 Drawing Sheets

BACKGROUND OF THE INVENTION

The invention of 'Ruby', a new and distintive cultivar of strawberry plant, is a result of the cross breeding between B1' (an unpatented J&P selection) and 'Selva' (U.S. Plant Pat. No. 5,266). The resulting plant was selected in a controlled breeding plot at J&P Research's cultivated field located in Naples, Fla. during the fruiting season of 1997–1998. It was designated as JPIby the inventor. This cultivar is botanically identified as *Fragaria xananassa Duch*. 'Ruby' has been propagated by runner and meristem culture in Naples, Fla. as well as in the commercial nurseries in United States and Canada. It has been trialed in the fields of growers in both North Carolina and Florida. 'Ruby' plant retains its distinctive characteristics and reproduces true to type in successive generations.

COMPARISON TO CLOSEST CULTIVARS

The commercial cultivar that we believe to be closest comparison to 'Ruby' in appearance from those known to us is 'Camarosa' (U.S. Plant Pat. No. 8,708). Both of them have the same isozyme banding pattern for phosphoglucose isomerase (PGI); leucine amino peptidase (LAP); and malate dehydrogenase (MDH). For the details see Table 1 isozyme analyses. However, there are several characteristics of 'Ruby' that are different from or not possessed by 'Camarosa'. Those are:

(1) Plant type: The fruiting plant of 'Ruby' is a very open and prostrate type plant with a long petiole, but 'Camarosa' is more compact and erect and a shorter petiole.

(2) Color: The fruit color of 'Ruby' (7.5R4/14) is distinctively lighter than that of 'Camarosa' (7.5R3/12 or 6.25R3/12);

(3) Shape: The fruit shape of 'Ruby' is conic to long conic in comparison to 'Camarosa' which is a more flat shaped fruit.

(4) Bracts: Most of the leaves of 'Ruby' have very distinctive bract leaflets on the petiole, whereas there are none on 'Camarosa'.

(5) Firmness: The fruit firmness of 'Ruby' is distinctive firm (517 gram per 5 mm diameter plunger tip) even firmer than 'Camarosa' (485 gram per 5 mm diameter plunger tip).

(6) Flavor: The fruit flavor of 'Ruby' (11.5 degree Brix) is distinctively sweeter than 'Camarosa' (9.8 degree Brix) by the Brix measurement.

(7) Calyx: The fruit calyx of 'Ruby' is larger and distinctive indent in comparison to those of 'Camarosa' which is smaller and more even or slight indent.

TABLE 1

Isozyme in leaf extracts by electrophoresis for 'Ruby', 'Camarosa'.

| | Ruby | Camarosa |
|---|---|---|
| PGI | A2 | A2 |
| LAP | B3 | B3 |
| MDH | C2 | C2 |

All isozyme analyses were conducted using leaf tissue. Reference: J. Amer. Soc. Hort. Sci. 106:684-687,(1981); USDA Forest Service General Technical Report PSW-64, (1982); and Tanksley,S.D. and Orton, T.J. Isozymes in Plant Genetics and Breeding, Part A, pp. 469–516 (Elsevier Science Publishers B.V.,1984).

DESCRIPTION OF THE NEW CULTIVAR

Figure 1:
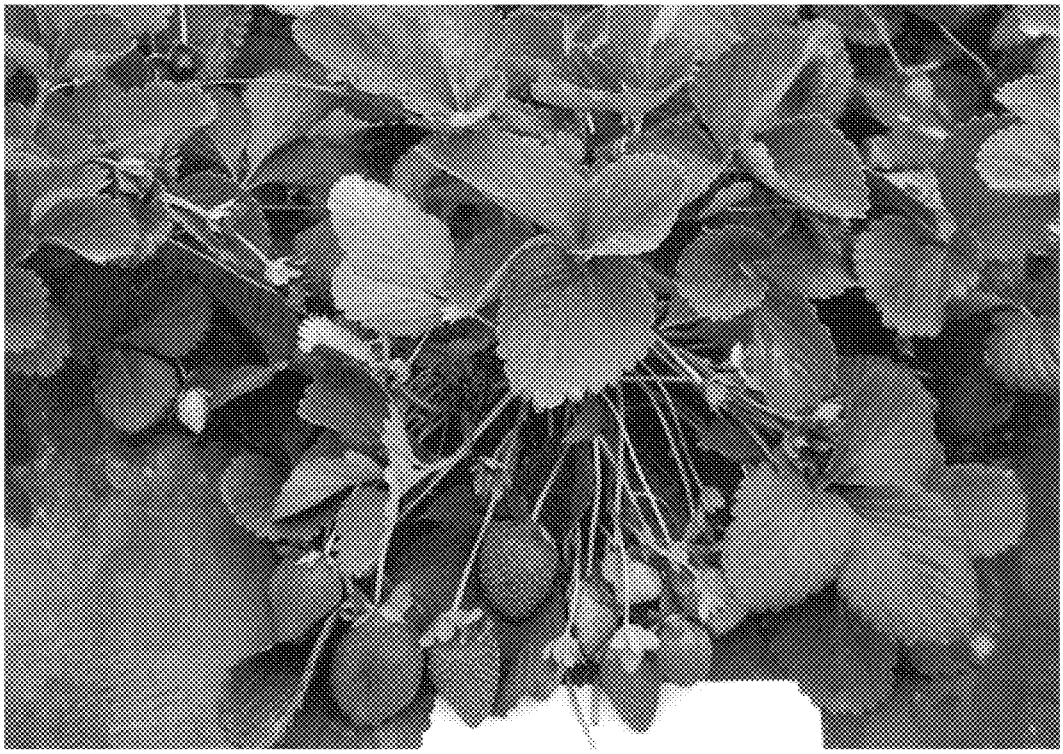
FIG. 1 shows the general flowering and fruiting characteristics of the plants during mid-season fruit production in Florida.
Figure 2:
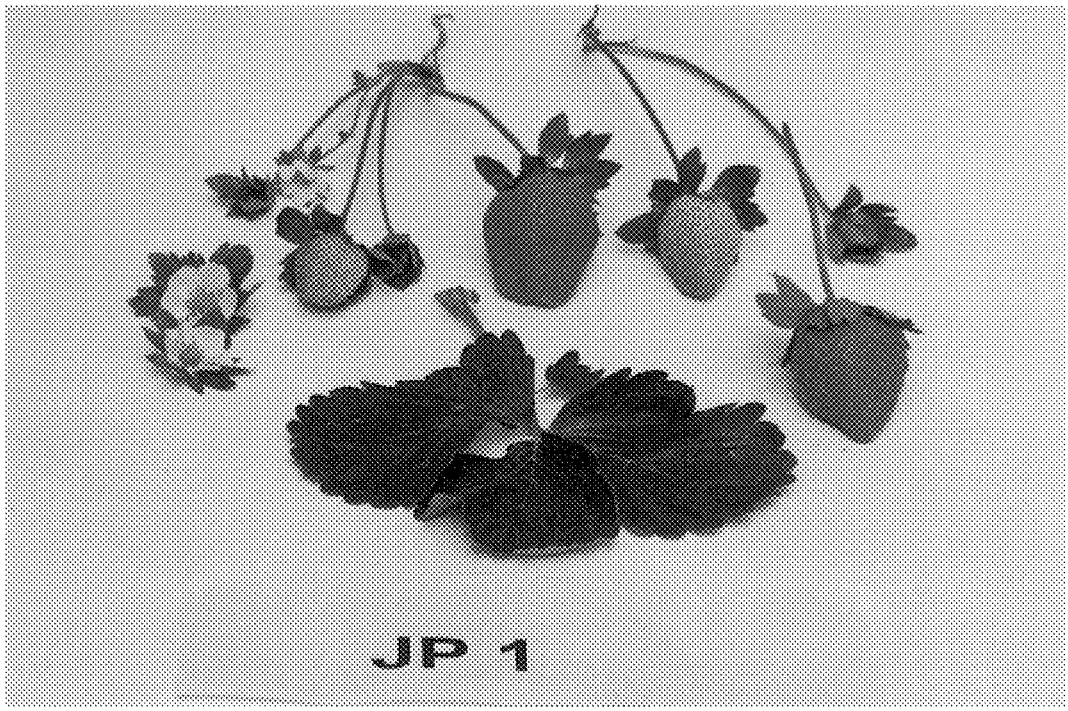
FIG. 2 depicts a) a typical mature compound leaf, b) a representative complete flower in mid-season, c) a fruiting truss including different stages of fruiting and flowering, and d) a typical mature fruit.

'Ruby' is a new and distinctive short-day type strawberry cultivar which is the result of a cross breeding between J&P selection 'B1' (an unpatented J&P selection) and 'Selva'. The female parent 'B1' possesses the distinguishing characteristics of its open plant type, low chilling requirement, long fruit stem, easy harvesting characteristics, high yield, large size, good shape, glossy color, good firmness, very juicy, good flavor and anthracnose tolerant. The male parent 'Selva' possesses the distinguishing characteristics of day neutrality or early production, high yields, large size, and firm fruit. The novel cultivar 'Ruby' resembles the female parent in possessing the characteristics of open plant type, low chilling requirements, long fruit stem, good shape, very glossy color, very juicy fruit and resemble the male parent in possessing the characteristics of high yield, large fruits and firm fruits. 'Ruby' obtains partial earliness from the male parent. 'Ruby' is superior to both parents in having higher yield, larger fruit size, firmer fruit, redder color of the skin and flesh and sweeter fruit and more aromatic. 'Ruby' is intermediate to its parents 'B1' and 'Selva' in anthracnose tolerant and early production.

'Ruby' is a semi-early fruiting cultivar, which has performed well in trials in Florida during the the1998–99 fruiting season. It is competitive with 'Camarosa' and 'Sweet Charlie' (U.S. Plant Pat. No. 8,729) the two most important cultivars grown in Florida at this time. 'Ruby' produces very firm fruits, which are firmer than those of 'Camarosa' and much firmer than those of 'Sweet Charlie'. The flavor of 'Ruby' is sweeter than 'Camarosa' and 'Sweet Charlie', which is reflected by the Brix Measurement. Fruit maturity is similar earliness to 'Camarosa', but later than 'Sweet Charlie', In general, yields from 'Ruby' are higher than those of 'Camarosa' but less than those of 'Sweet Charlie'.

However, 'Ruby' is more susceptible to powdery mildew disease, so it requires more attention in culture practices.

The distinctive characteristics of this new strawberry cultivar, described in detail below were observed upon its discovery and throughout the repeated test periods.

PLANTS AND FOLIAGE

The plants and foliage characteristics of 'Ruby' were collected about 4 month after planting the plants in fruiting field are listed in Table 2.

TABLE 2

Plant & Foliage Characteristics for 'Ruby'

Plant:
- *Average size.*—Height (mm): 275. Diameter (mm): 400.
- *Shape.*—Open and prostrate.
- *Density.*—Open.
- *Vigor.*—Strong.
- *Root initiation.*—Fast rooting, about 2 days to 5 days.

Foliage:
- *Terminal leaflet.*—Length (mm): 70. Width (mm): 71.
- *Shape of terminal leaflet.*—Orbicular with serrulate margin.
- *Color* (*Munsell color charts*).—Abaxial: 5GY 5/8. Adaxial: 5GY 6/4.
- *Leaf pubescence.*—Moderate to sparse and direction is acropetal.
- *Serrations number of terminal leaflets* (*mean*).—22.5.
- *Petiole.*—Length (mm): 199. Diameter (mm): 2.5. Color (Munsell color charts): 5GY 7/10. Pubescence: Heavy and direction is acropetal.
- *Petiolule.*—Length (mm): 11. Diameter (mm): 2. Color (Munsell color charts): 5GY 7/8.
- *Base angles of terminal leaflets*(*half blade*) (*degree*).—66.
- *Bract leaflet position* (*distance from base to bract/petiole length*).—0.73.
- *Stolons.*—Number: Many. Anthocyanin coloration: Moderate. Thickness (diameter, mm): 3. Pubescence: Moderate to sparse and the direction is acropetal.

RESISTANCE TO DISEASE AND STRESS

'Ruby' is a vigorous plant and similar in vigor to 'Camarosa' and 'Sweet Charlie'. 'Ruby' is more tolerant to anthracnose crown rot than 'Camarosa' and more tolerant to Botrytis than 'Sweet Charlie'. However, 'Ruby' is highly susceptible to powdery mildew. 'Ruby' is tolerant to rain cracking, moderately tolerant to high and low temperature. It generally does not have exposure to drought under our growing conditions.

FLOWERING AND FRUITING CHARACTERISTICS

The distinguishing flowering and fruiting characteristics of 'Ruby' plants were collected about 4–5 month after planting the plants are presented in Table 3. The flowers are self-fertile and pollination is very good. The Canadian-produced 'Ruby' plants typically begin to harvest about eight weeks after planting in Florida commercial production areas.

TABLE 3

Flower and Fruit Characters for 'Ruby'

Bud: At the stage of largest size, 1 day before flower opens.
- *Diameter* (*mm*).—20.
- *Length* (*mm*).—16.
- *Color* (*Munsell color charts*).—Upper: 5GY 7/8. Base: 7.5GY 5/4.

Flower: At fully open stage, 1 day after starting to open.
- *Diameter* (*mm*).—31.
- *Height* (*mm*).—95–125.
- *Number of flower/cluster.*—Average 3.
- *Fragrance.*—None.

Bloom time and period in specific location: Observed at the research plots of J&P Research Inc. In Naples, Fla. on plants planted mid-October.

Approximate date of bud burst, bloom time & duration: The earliest buds open starting 4 weeks after the plant were planted. Plants bloom from November until May.

Petals:
- *Length* (*mm*).—13.
- *Width* (*mm*).—13.
- *Shape.*—Obtuse. Apex Obtuse. Base Obtuse.
- *Color* (*no color chart given*).—White.
- *Texture.*—Tender.
- *Margin.*—Entire.
- *Number.*—Mean About 7. Range 9-May.

Sepals:
- *Length* (*mm*).—12.
- *Width* (*mm*).—5.
- *Shape.*—Oblanceolate. Apex Acute. Base Cuncate.
- *Color* (*Munsell color charts*).—Abaxial 7.5GY4/4. Adaxial 7.5GY 5/4.
- *Number.*—Mean About 14. Range 18-Oct.

Reproductive organs:
- *Stamens.*—Number 25–40. Length (mm) 2.5–5. Color (Munsell color charts) 5Y 8/10.
- *Pistils.*—Number & location About 200–300 pistils attached on the surface of the receptacle. Length (mm) 1–1.5. Color (Munsell color charts) 2.5GY 8/12.

Fruit shape: Conic to Long conic.

Fruit size & color:

*Development stage.*—Green fruit: At maximum size about 1–2 days before starting to turn to pink. Size: length (mm): 37. diameter (mm): 27. color (Munsell color charts): exterior: 2.5GY 8/4. flesh: White (no color chart given). Pink fruit: About 1–2 days before red. size: length (mm): 43. diameter (mm): 34. color (Munsell color charts): exterior: 7.5R 5/14. flesh: 7.5R 5/12. Ripe fruit-red: About 1–2 days after pink. size: length (mm): 45. diameter (mm): 38. weight (gram/fruit): Average: 16.2. Primary: 29.2. color (Munsell color charts): exterior: 7.5R 4/14. flesh: 7.5R 5/14. Red color from tip to shoulder.

Peduncle:

*Of flowers.*—Length (mm): 13.3. Diameter (mm): 3. Color (Munsell color charts): 5GY 7/8.

*Of fruits.*—Length (mm): 18.3. Diameter (mm): 4. Color (Munsell color charts): 5GY 6/8.

Pedicel:

*Of flowers.*—Length (mm): 4.3. Diameter (mm): 1.5. Color (Munsell color charts): 5GY 7/6.

*Of fruits.*—Length (mm): 5. Diameter (mm): 2. Color (Munsell color charts): 5GY 6/6.

Seeds:

*Number* (*mean*).—primary fruit: 385. secondary fruit: 265.

*Shape.*—Oblong.

*Size.*—length (mm): 1–1.5. diameter (mm): 0.5–1.

*Color* (*Munsell color charts*).—Most Yellow 5Y 8/10, some Red 10 R 5/10.

Calyx position: Indent/slight neck.

Seed position: Even/some raised.

The yield of 'Ruby' are compared below with those of 'Camarosa' and 'Sweet Charlie' in Table 4.

TABLE 4

| | | Ruby | Camarosa | S. Charlie |
|---|---|---|---|---|
| Yield (gram/plt) | December | 73 | 6 | 77 |
| | January | 122 | 97 | 145 |
| | February | 53 | 73 | 110 |
| | March | 286 | 279 | 333 |
| | Dec–Mar | 534 | 455 | 674 |
| Size (gram/fruit) | Average | 16 | 28 | 15 |
| | Primary | 29 | 29 | 24 |

TABLE 4-continued

| | | Ruby | Camarosa | S. Charlie |
|---|---|---|---|---|
| Firmness (Fruit Pressure Tester) (gram per 5 mm diameter plunger tip) (Higher value firmer fruit) | mean | 517 | 485 | 437 |
| | range | 490–550 | 350–550 | 283–525 |
| Soluble Solids a.k.a. Soluble Solids (degree Brix) | mean | 11.5 | 9.8 | 9.5 |
| | range | 7–14.5 | 6–12.3 | 7.2–14 |
| Skin color (Munsell color charts) | | 7.5R 4/14 | 7.5R 3/12–6.25R 3/12 | 7.5R 4/14 |

Data shown in Table 4 were collected during the 1998–1999 fruiting season. The plants for the data came from meristem cultured plants produced in Florida, which were then increased in Canadian nurseries, and grown on three different farms in Plant City, Fla. during the 98/99 fruiting season.

Yield of 'Ruby' is less than that of 'Sweet Charlie' but higher than that of 'Camarosa'. The fruit size of the primary fruit of 'Ruby' is similar to that of 'Camarosa', but larger than that of 'Sweet Charlie'. The fruit of 'Ruby' is firmer than that of 'Camarosa' and much firmer than that of 'Sweet Charlie' as measured by Fruit Pressure Tester equipped with a 5 mm diameter plunger tip. The sugar content or sweetness, measured as soluble solids, of 'Ruby' is higher than those of 'Camarosa' and 'Sweet Charlie' as measured by Sugar/Brix and the flavor of 'Ruby' is very sweet. The fruit skin color of 'Ruby' is similar to that of 'Sweet Charlie' but not as dark as that of 'Camarosa'. The 'Ruby' finish is very glossy and very attractive. The flesh color of 'Ruby' fruit is about the same as the skin and only slightly less intense. The 'Ruby' calyx is larger compared to those of 'Camarosa' and 'Sweet Charlie' and positioned indent to the base of the fruit. Seed placement of 'Ruby' is even with the fruit skin with some raised as that of 'Sweet Charlie' and less indent than that of 'Camarosa'.

Because of its high yield and excellent fruit quality, this cultivar is recommended for fresh market in the Southeastern United States.

We claim:

1. A new and distinct cultivar of strawberry plant named 'Ruby', as herein described and illustrated.

* * * * *